United States Patent [19]
Abrams et al.

[11] Patent Number: 5,112,954
[45] Date of Patent: May 12, 1992

[54] METHOD OF ENHANCING THE EFFECT OF CYTOTOXIC AGENTS

[75] Inventors: Paul G. Abrams, Seattle; Ananthachari Srinivasan, Kirkland; Vivekananda M. Vrudhula, Mountlake Terrace, all of Wash.

[73] Assignee: NeoRx Corporation, Seattle, Wash.

[21] Appl. No.: 176,851

[22] Filed: Apr. 4, 1988

Related U.S. Application Data

[63] Continuation-in-part of Ser. No. 161,174, Feb. 26, 1988, abandoned.

[51] Int. Cl.$^5$ ............... C07K 17/02; A61K 39/44
[52] U.S. Cl. ............... 530/391.9; 530/391.5; 530/388.85; 530/388.8; 424/85.8; 424/85.91
[58] Field of Search ............... 530/390, 391, 388; 424/85.8, 85.91

[56] References Cited

U.S. PATENT DOCUMENTS

| | | | |
|---|---|---|---|
| 4,093,607 | 6/1978 | Sela et al. | 530/391 |
| 4,302,386 | 11/1981 | Stevens | 424/88 |
| 4,494,547 | 1/1985 | Myers | 128/659 |
| 4,581,349 | 4/1986 | Wright | 514/81 |
| 4,609,659 | 9/1986 | Hartman | 514/255 |
| 4,620,971 | 11/1986 | Hou | 424/1.1 |
| 4,624,846 | 11/1986 | Goldenberg | 424/1.1 |
| 4,628,047 | 12/1986 | Sakurai et al. | 514/34 |
| 4,647,588 | 3/1987 | Engelhardt et al. | 514/603 |
| 4,654,369 | 3/1987 | Saari | 514/535 |
| 4,659,839 | 4/1987 | Nicolotti et al. | 548/546 |
| 4,671,958 | 6/1987 | Rodwell et al. | 424/85.91 |
| 4,867,962 | 9/1989 | Abrams | 424/1.1 |

FOREIGN PATENT DOCUMENTS

| | | |
|---|---|---|
| 0186252 | 7/1986 | European Pat. Off. |
| 197386 | 10/1986 | European Pat. Off. |
| 306943 | 3/1989 | European Pat. Off. |
| 2120941 | 12/1983 | United Kingdom |

OTHER PUBLICATIONS

Blair et al (1983) J. Immunol. Methods 59:129-143.
Heindel et al (1987) J. Pharm. Sci 76(5):384-386.
Gallego et al. (1984) Int. J. Cancer 33:737-744.
Hamilton et al (1983) Biochem. Pharmacol. 34(14):2583-2586.
Tsutsui et al (1986) Int. J. Radiation Oncol. Biol. Phys. 12:1183-1186.
Nori et al., *Cancer Investigation* 2(4), pp. 321-330 (1984), "Radiosensitizers and Protectors".
DeVita et al. editors, *Important Advances in Oncology* 1986, pp. 146-157, "Role of Glutathione in Primary Drug Resistance and Cross-Resistance".
Glover et al., *J. Clin. Onc.*, vol. 4, No. 4 (Apr.), 1986, pp. 584-588, "WR-2721 Protects Against the Hematologic Toxicity of Clyclophosphamide: A Controlled Phase II Trial".
Russo et al, *Cancer Treatment Reports*, vol. 69, No. 11, Nov. 1985, pp. 1293-1296, "Potentiation and Protection of Doxorubicin Cytotoxicity by Cellular Glutathione Modulation".
Russo et al, *Cancer Research* 46; (Jun. 1986), pp. 2845-2848, "Selective Modulation of Glutathione Levels in Human Normal versus Tumor Cells and Subsequent Differential Response to Chemotherapy Drugs".
Palcic et al, *Radiation Research* 100 (1984), pp. 340-347, "The Effect of Misonidazole as a Hypoxic Radiosensitizer at Low Dose".

(List continued on next page.)

*Primary Examiner*—Jeffrey E. Russel
*Assistant Examiner*—Kay Kim

[57] ABSTRACT

The activity of cytotoxic agents on target cells is enhanced through administration of a sensitizing agent to a patient prior to or simultaneously with administration of the cytotoxic agent. One or both of the two types of agents are attached to antibodies specific for the desired target cells, thereby enhancing the cytotoxic effect on target cells compared to non-target cells. The sensitizer and/or the cytotoxic agent may be attached to monoclonal antibodies specific for cancer cells to selectively eradicate the cancer cells while minimizing toxicity toward normal tissues.

9 Claims, 2 Drawing Sheets

OTHER PUBLICATIONS

Fitzpatrick, D. A., Cancerlit Abstract of *Diss. Abstr. Int.* (Sci), 47(8):3336, 1987, "The delivery of radiosensitizers to hypoxic tumor cells using monoclonal antibodies".

Borlinghaus et al., Biosis Abstract of *Cancer Res.* 47(5), 1987, pp. 4071–4075, "Radiosensitizer conjungation to the carcinoma 19-9 monoclonal antibody".

Heindel et al., Biosis Abstract of *J. Pharm. Sci.* 76(5), 1987, pp. 384-386, "Macromolecular attachment as a metabolic stabilizer for a labile radiosensitizer".

Varghese, A. J. Biosis *Biochem. Biophys. Res. Commun.* 112(3), 1983, pp. 1013-1020, "Glutathione conjugates of misonidazole".

Souchek et al., *Chemical Abstracts*, vol. 106, No. 8, Feb. 23, 1987, p. 487, ref. No. 65711, "Sensitization of tumor target cells to cytolysis by murine macrophage cytolytic factor by drugs inhibiting DNA RNA and protein synthesis".

Arrick et al., Medline Abstract of *J. Clin. Invest.*, Feb. 1983, 71(2), pp. 258-267, "Inhibition of glutathione synthesis augments lysis of murine tumor cells by sulfhydryl-reactive antineoplastics".

Mitchell et al., Cancerlit Abstract of Chemical Modifiers of Cancer Treatment, Oct., 20-24, 1985, Clearwater, Fla., Abstract 2-16, 1985, "The relationship of SR-2508 sensitizer enhancement ratio to cellular glutathione levels in human tumor cell lines" (meeting abstract).

METHOD OF ENHANCING THE EFFECT OF CYTOTOXIC AGENTS

CROSS REFERENCE TO RELATED APPLICATIONS

This application is a continuation-in-part of U.S. application Ser. No. 161,174, filed Feb. 26, 1988 now abandoned.

TECHNICAL FIELD

The present invention relates to methods for delivering sensitizing agents specifically to target cells such as tumor cells. The sensitizing agents render the tumor cells more susceptible to eradication by cytotoxic agents administered simultaneously with or subsequent to administration of the sensitizing agent.

BACKGROUND

Much effort has been directed to developing methods for treating the various forms of cancer. A number of treatment methods, including radiotherapy or chemotherapy with one or more drugs, toxins, or therapeutic proteins (e.g., interleukin-2) have been developed. Efforts to enhance the patient's immune response to cancer cells (e.g., an antibody-dependent cellular cytotoxicity response) also have been reported. Unfortunately, many of the current therapeutic procedures have met with mixed results, and side effects caused by the action of therapeutic agents on normal cells within the patient's body are associated with many of these procedures. Indeed, the toxic or damaging effect of various therapeutic agents on normal tissues is often the dose-limiting factor during therapy. A need remains for more effective treatments for cancer, especially treatments which minimize side effects caused by action of the therapeutic agents on non-tumor tissues within a patient.

SUMMARY OF THE INVENTION

The present invention provides immunoconjugates comprising a sensitizing agent bound through a suitable linker such as a cleavable linker to a targeting protein such as an antibody which is specific for target cells within a human or mammalian host Upon administration of the immunoconjugate to the host, the sensitizing agent is delivered to the target cells and then is released in biologically active form from the antibody The sensitizing agent enhances the effectiveness of a cytotoxic agent administered simultaneously with or after administration of the immunoconjugate comprising the sensitizer The target cells may be cancer cells such as melanoma cells or lung, breast, or colon carcinoma cells, and the antibody may be a monoclonal antibody specific for the cancer cells Also provided by the present invention are methods of specifically increasing the cytotoxic effect of a cytotoxic agent on target cells compared to non-target cells within a human or mammalian host, comprising administering to said host a sensitizing agent and a cytotoxic agent wherein at least one of the sensitizing agent or cytotoxic agent is conjugated to an antibody specific for the target cells. When the biological activity of the sensitizing agent or the cytotoxic agent would be enhanced by release from the immunoconjugate, the linkage between the agent and the antibody is preferably cleavable at the target site. Methods of treating cancer also are provided.

DETAILED DESCRIPTION OF THE INVENTION

Figure 1:
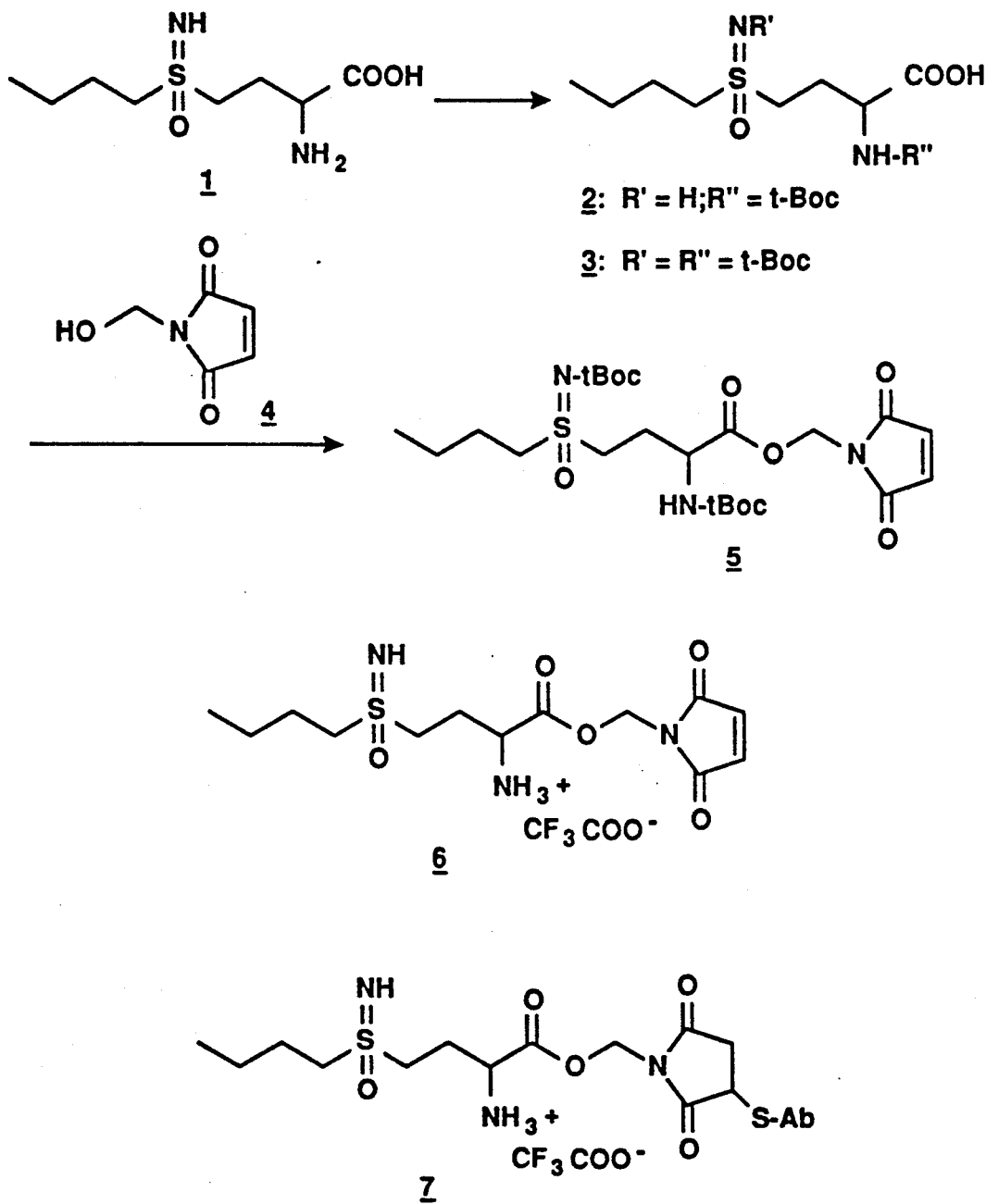
FIG. 1 depicts a synthesis scheme for linking the sensitizer buthionine sulfoximine to an antibody.

The present invention provides a method for selectively enhancing the action of cytotoxic agents against a particular type of target tissue compared to non-target tissues. The method comprises administering to a mammalian or human host a sensitizing agent and a cytotoxic agent wherein either the sensitizing agent or the cytotoxic agent or both are conjugated to a protein (such as an antibody) specific for a certain target site in vivo. An example of such a target site is a cancer site, which may comprise melanoma, lung carcinoma, breast carcinoma, or colon carcinoma cells, among others.

The sensitizing agent is an agent that enhances the effectiveness of the cytotoxic agent in eradicating cells. In general, sensitizers act by rendering cells unable to repair or withstand the second insult caused by the cytotoxic agent but do not themselves function as the cytotoxic agent. Thus, cells which have been contacted with both a sensitizing agent and a cytotoxic agent during therapy are more likely to be destroyed than are cells contacted by only one of the two types of agents. There are believed to be a large variety of mechanisms by which sensitizers render cells more susceptible to toxic molecules, such as interference with transport mechanisms, induction or repression of enzyme systems, or interference with cellular repair mechanisms. The agents are generally not very specific for a particular type of cells (e.g., tumor cells) and, therefore, enhance the sensitivity of both normal and malignant tissue. The resulting problem, which has been reported during past attempts at using sensitizers, is increased sensitivity of the malignant tissue, but at the expense of increased toxicity toward normal tissues.

A number of compounds which function as sensitizers to enhance the effectiveness of certain cytotoxic agents are known. See, for example, *Important Advances in Oncology* 1986, DeVita et al., editors, J.B. Lippincott Co., Philadelphia, pages 146–157 (1986), which reports contacting drug-resistant tumor cell lines in vitro with certain agents (e.g., buthionine sulfoximine or calcium channel blockers such as verapamil) to restore the sensitivity of the cells to certain cytotoxic drugs. U.S. Pat. No. 4,628,047 describes the use of the drug diltiazem to enhance the therapeutic activity of antitumor drugs such as doxorubicin, daunorubicin, and vinca alkaloids such as vincristine. The compounds metronidazole, misonidazole, certain 2-sulfamyl-6-nitrobenzoic acid derivatives (e.g., 2-(substituted sulfamyl)-6-nitrobenzoates or 2-(substituted sulfamyl)-6-nitrobenzamides), 2,6-disubstituted derivatives of 3-nitropyrazine, and certain isoindoledione compounds have been reported to function as sensitizers for therapeutic radiation. (See U.S. Pat. Nos. 4,647,588; 4,654,369; 4,609,659; and 4,494,547.)

Other drugs which may function as sensitizers include the drug S-2-(3-aminopropylamino) ethyl phosphorothioic acid (known as WR 2721) and analogs thereof. The drug WR 2721 is represented by the following formula:

$H_2N-(CH_2)_3-NH-(CH_2)_2-SPO_3H_2$

WR 2721. and its analogs, were developed to protect soldiers from the effects of radiation. These drugs are among the known "protecting agents" used to protect normal tissues during cancer therapy. In patients with cancer, there is evidence that WR 2721 may provide some protection to the bone marrow and other organs from some chemotherapeutic drugs such as alkylating agents and cis-platinum. This allows the use of higher doses of these drugs. It may also provide some protection of normal tissues from external beam radiation therapy. The use of WR 2721 as a protecting agent has been described by Glover et al. (J. of Clinical Oncology, Vol. 4, No. 4, Apr., 1986, pp 584-588) and Nori et al. (Cancer Investigation, Vol. 2, No. 4, 1984, pp 321-330.) Its effects on tumor sensitivity appear to be either negligible or perhaps, paradoxically, to sensitize the tumor as it protects normal organs. Thus, WR 2721 may function as a sensitizer for radiation and certain cytotoxic drugs, depending on such factors as the type of tumor to be eradicated.

The drug WR 2721 is believed to be selectively absorbed by normal tissues, whereas solid tumor tissues absorb relatively little of the drug. Certain derivatives of WR 2721 which are less hydrophilic more readily cross tumor cell membranes. (See Glover et al., supra, p 585). It may be advantageous to use these less hydrophilic derivatives when the drug is to be used as a sensitizer. In addition, attaching WR 2721 or derivatives thereof to a tumor-specific targeting protein may enhance uptake of the drug into tumor cells in those cases where the drug functions as a sensitizer.

WR 2721, and its analogs, may be administered as free drug prior to treatment of a patient with a conjugate of an antibody, or other targeting protein, and a radioactive substance capable of lethally damaging cells. Unlike external beam radiation that is directed at a particular site, where WR 2721 can protect normal tissues at a local site, circulating radioactivity in the form of a labeled protein conjugate delivers radiation to the total body and to all normal organs at variable amounts based upon relative accumulation at those sites. Compared to external beam radiation, intravenously administered radiation is a very low dose rate. Moreover, the dose is variable with time after administration. External beam radiation delivers its dose at a high, even rate to tumor and normal tissues. The local nature, and high, even dose rate of external beam radiation is very different from intravenous, internal low-dose rate radiation that exposes the patient to radiation continuously, generally from one hour to two weeks (depending on the half life of the radioisotope, the clearance rate of the radiolabeled conjugate, etc.), as occurs with radiolabeled antibodies or other targeting agents WR 2721 may be administered intravenously as a free drug with doses from 200 mg-2 gm/m² but preferably from 0.5-1 gm/m²; and immediately thereafter, the radiolabeled antibody is injected. WR 2721 may be administered subsequently to increase the protection of the marrow and normal tissues, depending on the half life of the radioisotope and the radiolabeled antibody, or fragment thereof.

Alternatively, protecting agents such as WR 2721 may be attached to one or more targeting proteins that bind to non-target tissues, so that the agent is delivered to non-target tissue(s) to be protected from a cytotoxic agent. For example, WR 2721 may be targeted to marrow stem cells by conjugating it to an antibody that binds to marrow stem cells. If WR 2721 increases tumor resistance when administered in its free form, and this may vary from tumor to tumor, targeting it to the marrow stem cell preserves the sensitivity of the tumor to the radiation and yet provides protection to the marrow.

Alternatively, the WR 2721 may be attached to a tumor-specific targeting protein instead of being administered as the free drug. The use of such conjugates is advantageous when the drug functions as a sensitizer with respect to the particular type of tumor to be treated and the cytotoxic agent to be administered.

Another application of WR 2721 and its analogs is to decrease the toxicity of toxin and drug conjugate of antibodies, fragments thereof, or other targeting proteins, to non-target organs that cross react with the targeting protein or nonspecifically accumulate the conjugate. For example, WR 2721, or its analogs, may decrease the hepatotoxicity of Pseudomonas exotoxin-antibody conjugates.

Administration of protecting agents reduces damage to non-target tissues, but generally does not completely eliminate the destruction of non-target (normal) cells. Thus, it may be desirable to additionally administer to the patient a substance that enhances proliferation of one or more types of non-target cells. Such substances include, but are not limited to, colony stimulating factors (CSF) which stimulate proliferation of cells within bone marrow Examples of these substances are erythropoietin, which acts on red blood cells, granulocyte-CSF, and granulocyte-macrophage-CSF.

In addition, some drugs that have cytotoxic effects under certain circumstances may be used as sensitizers when administered in conjunction with certain cytotoxic agents. For example, a particular drug which has cytotoxic effects at higher dosages may be effective as a sensitizer when administered at relatively low dosages. Thus, these agents may be administered at dosages below that required for effective cytotoxic action, but sufficient to enhance the effectiveness of a cytotoxic agent administered along with, or subsequent to, the sensitizer. Thus, in some instances the definition of a sensitizer includes a dosage, since at a higher dosage certain sensitizers (but not all) could function as the cytotoxic agent. Problems associated with administration of high dosages of certain cytotoxic drugs may be reduced when those drugs are used at lower dosages as the sensitizer instead. Examples of some of the many drugs which have cytotoxic effect at higher dosages but which may be used as the sensitizer in the present invention include doxorubicin, bleomycin, and platinum compounds such as cis-diaminodichloro platinum (cis-platin).

A number of cytotoxic agents that have a lethal effect on target cells within the patient, wherein the lethal effect may be enhanced by one or more sensitizing agents, may be used in the method of the invention. Included are radiation (whether the radiation therapy is delivered internally or administered by external means) and cytotoxic drugs. Examples of some of the many such drugs are nitrogen mustards such as L-phenylalanine nitrogen mustard (melphalan), anthracycline antibiotics such as daunorubicin and doxorubicin, platinum compounds such as cis-diamino dichloro platinum (cis-platin), and vinca alkaloids such as vincristine. Internally delivered radiation includes therapeutically effective radioisotopes injected into a patient. Such radioisotopes include, but are not limited to, the radionuclide metals $^{186}Re$, $^{188}Re$, $^{64}Cu$, $^{67}Cu$, $^{109}Pd$, $^{212}Bi$, $^{203}Pb$, $^{212}Pb$, $^{211}At$, $^{97}Ru$, $^{105}Rh$, $^{198}Au$, $^{199}Ag$, and $^{131}I$. These radioisotopes generally will be bound to carrier molecules (e.g., are in the form of a chelate-antibody conjugate) when administered to a patient. Examples of suitable internally delivered radiotherapeutic agents are the metal radionuclide chelates which are conjugated to antibodies as described in European Patent Application Publication No. 188,256. Radiation administered by external means includes external beam radiation such as cobalt therapy.

The choice of sensitizing agent depends on such factors as the particular type of tumor to be treated and the desired cytotoxic agent to be administered. For example, certain drugs have been reported to sensitize cells to therapeutic radiation, as discussed above. U.S. Pat. No. 4,628,047 reports the use of diltiazem (chemical name: d-3-acetoxy-cis-2,3-dihydro-5-[2-(dimethylamino) ethyl]-2-(p-methoxyphenyl)-1,5-benzothiazepin-4(5H)-one) to enhance the sensitivity of a variety of types of cancer cells toward cytotoxic agents such as doxorubicin and the vinca alkaloid vincristine. DeVita et al. (supra) includes discussions of other pairings of sensitizers with certain cytotoxic drugs as well as expected differences in the susceptibility of different types of cancer cells to treatment with these agents. For example, BSO is thought to function as a sensitizer for drugs that have a cytotoxic effect that is enhanced by decreasing cellular glutathione levels. Additional combinations of sensitizers and cytotoxic agents may be identified through such methods as in vitro assays using cultured cells which correspond to the desired target cells (e.g., a specific cancer cell line). Assays for determining whether BSO is effective in lowering GSH levels in a particular type of cell line have been developed (*Cancer Treatment Reports*, Vol. 69, No. 11, pp 1293–1296 [1985]).

In accordance with the present invention, either the cytotoxic agent or the sensitizing agent or both is attached to a target-specific protein. The targeting protein delivers the agent attached thereto to a desired target site in vivo. Such proteins include those specific for receptors on the target cells. Targeting proteins suitable for use in the present invention include, but are not limited to, hormones and antibodies. The antibodies may be polyclonal or monoclonal, with monoclonal antibodies (MAbs) specific for target cells being preferred. A number of monoclonal antibodies that bind to a specific type of cell have been developed, including MAbs specific for tumor-associated antigens in humans. Among the many such MAbs that may be used are anti-TAC, or other interleukin-2 receptor antibodies; 9.2.27 and NR-ML-05 to the 250 kilodalton human melanoma-associated proteoglycan; NR-LU-10 to 37–40 kilodalton pancarcinoma glycoprotein; and OVB3 to an as yet unidentified tumor-associated antigen. Antibodies derived through genetic engineering or protein engineering may be employed as well. The antibody employed in the present invention may be an intact molecule, a fragment thereof, or a functional equivalent thereof. Examples of antibody fragments are F(ab')$_2$, Fab', Fab, and Fv fragments, which may be produced by conventional methods, or by genetic or protein engineering.

Whether just the sensitizing agent or the cytotoxic agent, or both, are conjugated to antibodies, only the desired target cells are exposed to both types of agents, and thus are rendered more susceptible to eradication than are non-target tissues When only the sensitizing agent is linked to a target-specific antibody, target and non-target cells are exposed to the cytotoxic agent which is administered to the patient, but only the target cells are exposed to both the sensitizer and the cytotoxic agent. When only the cytotoxic agent is attached to an antibody, both target and non-target cells are exposed to the sensitizing agent, but only the target cells are exposed to both types of agents When both types of agents are conjugated to antibodies, only the target cells are exposed to the agents.

When both types of agents are conjugated to antibodies, they may be attached to different antibodies that bind to the desired target cells; e.g., antibodies that recognize different epitopes on the target cells. For example, the MAbs 9.2.27 (Morgan, et al., Hybridoma, 1:17 [1981]) and NR-ML-05 (copending U.S. patent application Ser. No. 024,632, "Enhanced Production of Antibodies Utilizing Insolubilized Immune Complexes") recognize different epitopes of a 250 kilodalton melanoma-associated antigen. Methods of isolating two antibodies reactive with different epitopes on a particular type of target cell are known. One such method is presented in the copending patent application U.S. Ser. No. 024,632. Alternatively, the two agents may separately be conjugated to the same antibody. In yet another embodiment of the invention, the two agents may be reacted with an antibody such that the resulting immunoconjugate comprises both agents attached to the same antibody molecule.

In one embodiment of the invention, a sensitizing agent and a cytotoxic agent are attached to different antibody species, wherein each of the antibody species is reactive with a different epitope on the target site and the patterns of cross-reactivity for each antibody species are non-overlapping. Thus, the sensitizing agent and cytotoxic agent accumulate additively on the target tissue, but only one of the agents accumulates on each type of non-target tissue with which one of the antibodies cross-reacts. Pairs of antibody species having substantially non-overlapping patterns of cross-reactivity with normal tissues, and the use thereof, are further described in the copending U.S. patent application entitled "Functionally Specific Antibodies", attorney docket number 87-012, filed on even date herewith (issued as U.S. Pat. No. 4,867,962 on Sept. 19, 1989).

Different antibodies reactive with a target site of interest are screened by known immunohistochemical analysis procedures to determine the pattern of cross-reactivity with a variety of normal tissue samples, for each antibody species. One immunohistochemical assay procedure is described in Ceriani et al., *Cancer Research*, 47:532–540, Jan. 15, 1987. Two antibody species having substantially non-overlapping patterns of cross-reactivity (i.e., functionally specific antibodies) are thereby identified for use in the present invention. The statement that the patterns of cross-reactivity are non-overlapping means that the list of non-target tissues with which one antibody cross-reacts is completely or at least substantially different from the list of non-target tissues with which the other antibody species reacts. The use of functionally specific antibodies is advantageous because the incidence of both the cytotoxic agent and the sensitizing agent localizing on the same non-target tissue (through cross-reactivity of the antibodies to which the agents are attached) is minimized or eliminated.

Two monoclonal antibodies which may be used as functionally specific antibodies are TFS-2 (also designated herein as NR-LU-10) and TFS-4 (also designated NR-LU-11) which have been described by Varki et al., *Cancer Research*, 44:681-687 (1984) and Okabe et al. *Cancer Research*, 44:5273-5278 (1984). Both antibodies react with small cell lung cancer. Evaluation of cross-reactivity with a battery of normal tissue samples indicated that the only normal tissue type with which both antibodies reacted was thyroid, although each antibody bound to several additional normal tissues.

Another method for reducing uptake of antibodies into non-target tissues (e.g., through cross-reactive or nonspecific binding mechanisms) has been described in the copending U.S. patent application Ser. No. 107,136, entitled "Methods for Improved Targeting of Antibody, Antibody Fragments, Hormones, and other Targeting Agents, and Conjugates Thereof."

Thus, the present invention provides methods for selectively enhancing the eradication of target cells (e.g., cancer cells) compared to non-target cells within a patient. Specific delivery of one or both of the sensitizing agent and the cytotoxic agent to the desired target cells reduces toxicity to non-target cells, since the non-target (normal) cells are exposed to one (or none) of the agents, but not both. This is an important advantage, since toxicity caused by the action of a therapeutic agent on normal tissues is often a dosage-limiting factor for many treatment methods currently in use.

It is known that monoclonal antibodies are rarely 100% specific for a desired target site. For example, MAbs said to be specific for a certain antigen generally exhibit some cross-reactivity with and/or non-specific uptake into non-target tissues, even though a high percentage of the MAb localizes at the desired target site in vivo. Thus, the discussions of antibody specificity and the like presented herein are to be interpreted within the context of the understanding of those terms in the art. It is desirable to use a monoclonal antibody having as high a degree of specificity as possible for the target cells.

The procedure for attaching an agent to an antibody will vary according to the chemical structure of the agent. Antibodies are proteins that contain a variety of functional groups; e.g., carboxylic acid (COOH) or free amine ($-NH_2$) groups, which are available for reaction with a suitable functional group on an agent molecule to bind the agent thereto Alternatively, the antibody and/or agent may be derivatized to expose or attach additional reactive functional groups The derivatization may involve attachment of any of a number of linker molecules such as those available from Pierce Chemical Company, Rockford, Ill. (See the Pierce 1986-87 General Catalog, pages 313-354 ) Alternatively, derivatization may involve chemical treatment of the antibody; e.g., glycol cleavage of the sugar moiety of the glycoprotein antibody with periodate to generate free aldehyde groups. The free aldehyde groups on the antibody may be reacted with free amine or hydrazine groups on an agent to bind the agent thereto. (See U.S. Pat. No. 4,671,958.) Procedures for generation of free sulfhydryl groups on antibodies or antibody fragments (e.g. by reduction of disulfides to generate thiol groups) also are known. (See U.S. Pat. No. 4,659,839.) The free thiol groups may, for example, be reacted with an activated double bond (e.g. the double bond of a maleimide group on a linker) to produce a thioether bond. Many procedures and linker molecules for attachment of various compounds (including radionuclide metal chelates, toxins, and drugs) to proteins such as antibodies are known. See, for example, European Patent Application Publication No. 188,256; U.S. Pat. Nos. 4,671,958; 4,659,839; 4,414,148; 4,699,784; 4,680,338 4,569,789; and 4,590,071; and Borlinghaus et al. (*Cancer Research*, 47:4071-4075, Aug. 1, 1987).

In one embodiment of the invention, a single antibody species is reacted (either simultaneously or sequentially) with both the cytotoxic agent and the sensitizing agent so that both agents are attached to the same antibody molecule. The methods of attaching the two agents to the antibody will depend on the chemical structure of the agents.

A problem associated with some methods of linking certain compounds to antibodies is that the biological activity of the compound (e.g., drug, toxin, etc.) may be reduced when the compound is attached to the antibody. When such compounds are conjugated to an antibody through a stable covalent bond, for example, release of the compound in its free, maximally active form at the target site generally would not be expected to occur. For example, in the immunoconjugates comprising the radiosensitizer misonidazole covalently bound to a monoclonal antibody described in Borlinghause et al. supra, the in vivo activity of misonidazole is expected to be reduced when compared to the free drug.

Therefore, immunoconjugates comprising linkages which are cleavable in the vicinity of the target site are preferred for use in the present invention when the desired biological activity of the agent (i.e., the sensitizing activity or the cytotoxic activity) would be diminished if it were not released from the antibody. The agent thus is delivered to the target site by the antibody, then released in biologically active form from the antibody. Cleaving of the linkage to release the sensitizer or cytotoxic agent from the antibody may be prompted by enzymatic activity or conditions to which the immunoconjugate is subjected either inside the target cell or in the vicinity of the target site. When the target site is a tumor, a linker that is cleavable under conditions present at the tumor site (e.g., when exposed to tumor-associated enzymes or acidic pH) may be used. A number of different cleavable linkers have been described previously. The mechanisms for release of an agent from these linker groups include cleavage by reduction of a disulfide bond, by irradiation of a photolabile bond, by hydrolysis of derivatized amino acid side chains, by serum complement-mediated hydrolysis, and acid-catalyzed hydrolysis. U.S. patent application Ser. No. 07/127,656, filed Dec. 2, 1987; subsequently abandoned in favor of continuation-in-part application U.S. Ser. No. 07/454,295, filed Dec. 19, 1989, discloses immunoconjugates comprising linkers of specified chemical structure, wherein the linkage is cleaved in vivo, releasing the compound (radiotherapeutic agent, drug, toxin, etc.) in its native form. The linker is susceptible to cleavage at mildly acidic pH, and is believed to be cleaved during transport into the cytoplasm of a target cell, thereby releasing the biologically active compound inside a target cell. U.S. Pat. No. 4,671,958 includes a description of immunoconjugates comprising linkers which are cleaved at the target site in vivo by the proteolytic enzymes of the patient's complement system. Descriptions of additional cleavable linkage systems are presented in the Examples section below. The immunoconjugates produced by the procedures of Examples I and V are believed to be internalized (i.e., transported into the cytoplasm of a target cell, e.g., via an endosome). Enzymes within target tumor cells are expected to cleave the bond between the sensitizing agent and the antibody, thereby releasing the sensitizer in biologically active form within target cells.

In accordance with the present invention, the sensitizer (in unconjugated or immunoconjugate form) is administered to a patient prior to or simultaneously with administration of the cytotoxic agent (in unconjugated or immunoconjugate form). The amount of each agent administered is such that the combination of the two types of agents is therapeutically effective. The dosages will vary in accordance with such factors as the type and number of tumors, the type of agents being administered, and whether one or both agents are linked to antibodies.

In one embodiment of the invention, a method for treating cancer is provided. A cytotoxic agent effective against the type of cancer with which a patient is afflicted is administered to the patient simultaneously with or subsequently to administration of a sensitizer which effectively sensitizes the target cancer cells toward the cytotoxic effects of the cytotoxic agent. One or both of the sensitizer and the cytotoxic agent are attached to an antibody (preferably a MAb) specific for the target cancer cells. Each immunoconjugate comprises a cleavable linkage when release of the sensitizer or cytotoxic agent from the antibody at the target site is desired.

Those skilled in the medical oncology arts will readily appreciate that the doses and schedules of the free sensitizer, the conjugated sensitizer, the free drug and/or the conjugated drug will vary depending on toxicity, antigen expression on tumor, the distribution of target antigen(s) on normal tissues and the relative susceptibilities of tutors and normal cross reactive tissues to the drug and/or sensitizer. These parameters may be determined for each system by well-established procedures and analysis e.g., in phase I, II and III clinical trials.

The following examples are provided for purposes of illustration and are not to be construed as limiting the scope of the present invention.

EXAMPLE I

Attaching the Sensitizer BSO to an Antibody

Buthionine sulfoximine (BSO) is a synthetic amino acid that inhibits gamma-glutamylcysteine synthetase and leads to a marked decrease of glutathione (GSH) in cells. BSO is available from Chemical Dynamics Corporation, South Plainfield, N.J. A synthetic scheme for conjugating BSO to antibody is shown in FIG. 1 and described below.

Preparation of N,N'-Bis(t-butoxycarbonyl)buthionine sulfoximine 3: To a stirred solution of buthionine sulfoximine 1 (1.6 g, 5 mmol) in THF-H$_2$O (1:1, 25 mL) was added Et$_3$N (750 uL, 1.1 equiv) followed by di-tert-butylpyrocarbonate (4.5 g, 4.1 equiv). The clear biphasic mixture was stirred for 15 h. At the end tetrahydrofuran was evaporated in vacuo and MeOH (15 mL), Et$_3$N (750 ul) were added and to the homogeneous solution were added portions of di-tert-butylpyrocarbonate (15.25 g, 14 equiv, 2 equiv/48 h during the first 96 h and then 5 equiv/48 h during the later 96 h) over a period of 8 days. Reversed phase TLC, MeOH-H$_2$O (7:3) showed mainly two spots (RF=0.7 and 0.4) after spraying and heating with ninhydrin. Acetic acid (1 mL) was added to the reaction mixture and volatiles were evaporated in vacuo and the residue reevaporated with toluene in vacuo. The resulting oil was dissolved in MeOH and water was added to slight turbidity. It was then charged onto a C$_{18}$ column equilibrated with MeOH-H$_2$O (3:7) and eluted with MeOH-H$_2$O (3:7, 500 mL), MeOH-H$_2$O (2:3, 250 mL), MeOH-H$_2$O (1:1, 200 mL), MeOH-H$_2$O (3:1, 300 mL) and finally with MeOH (300 mL) collecting fractions of 75 mL size. Fractions containing N-t-butoxycarbonylbuthionine sulfoximine 2 were combined and evaporated in vacuo to give 1.05 g as a powder. $^1$H NMR (CDCl$_3$) δ8.1 (2H, exchangeable with D$_2$O, br's), 5.8 (1H, exchangeable with D$_2$O, br's), 4.3 (1H, m), 3.2 (4H, m), 2.3 (2H, m), 2.0–0.8 (16 H, m). Fractions containing N,N'-bis(t-butoxycarbonyl)buthionine sulfoximine 3 were combined and evaporated in vacuo to give 450 mg as a foam. $^1$H NMR (CDCl$_3$) δ6.0–5.5 (2H, exchangeable with D$_2$O, br's), 4.40 (1H, m), 3.4 (4H, m), 2.5–2.2 (2H, m), 1.8 (2H, m), 1.48, 1.45 (18 H, 2xS), 0.97 (3H, t, J=7Hz). $^{13}$C NMR (CDCl$_3$) δ176.3, 158.9, 156.4, 80.8, 80.3, 51.5 51.3, 48.1, 48.0, 28.3, 28.1, 27.9, 25.5, 24.3, 24.1, 21.5, 13.5.

Preparation of N,N'-Bis(t-butoxycarbonyl)sulfoximine (maleimido)methyl ester 5: A solution of 3 (290 mg, 0.7 mmol) in CH$_2$Cl$_2$ (3 mL) under argon was cooled to 0° C. and Et$_3$N (100 ul) was added. After 10 min. isobutyl chloroformate (120 ul) was added dropwise via a syringe. The solution was stored at 0° C. under argon for 1 h. A solution of N-hydroxymethyl-maleimide 4 (89 mg, 0.7 mmol) in CH$_2$Cl$_2$ (2 mL) was then added dropwise and the amber colored suspension was stirred at 0° C. for 30 min at which time TLC, silica gel, MeOH-CH$_2$Cl$_2$ (1:19) indicated completion of the reaction. The reaction mixture was diluted with CH$_2$Cl$_2$ (15 mL) and partitioned between water (10 mL) and CH$_2$Cl$_2$. Organic layer was dried (Na$_2$SO$_4$), filtered, evaporated in vacuo. The residue (370 mg) was subjected to flash chromatography with MeOH-CH$_2$Cl$_2$ (1:19) on 1×15 cm silica gel column. Fractions containing N,N'-bis(t-butoxycarbonyl)buthionine sulfoximine(maleimido)-methyl ester 5 were combined and evaporated in vacuo to give a pale yellow oil (230 mg, 62%). $^1$H NMR (CDCl$_3$) δ6.8, (2H, S), 5.6 (24, m), 5.2 (1H, m), 4.3 (1H, m), 3.5–3.1 (4H, m), 1.5–2.1 (2H, m), 1.8 (2H, m), 1.48, 1.45 (18H, 2S), 0.95 (3H, t, J=7.0 H2).

Preparation of Sulfoximine (maleimido)methyl ester 6: A solution of 5 (71 mg) in CH$_2$Cl$_2$ (350 uL) was treated with anhydrous TFA (50 uL). Pale yellow solution was stored at ambient temperature overnight. TLC, silica gel, MeOH-CHCl$_3$ (1:9) and n-BuOH-AcOH-H$_2$O (3:2:1) indicated completion of the reaction. Volatiles were evaporated. The crude product was triturated with Et$_2$O (2×5 mL) and washings discarded. $^1$H NMR (D$_2$O) of the residue showed δ 6.8 (2H, S), 5.6 (2H, m), 4.6 (1H, m, partly buried under H$_2$O peak), 3.6–3.2 (4H, m), 2.4–2.2 (2H, m), 1.8–1.5 (2H, m), 1.4–1.2 (2H, m), 0.8 (3H, t, J=7.0 Hz) which is consistent with the proposed structure.

The BSO derivative 6 is conjugated to a monoclonal antibody that recognizes a tumor-associated antigen. One such antibody is NR-ML-05 that recognizes a 250 Kd glycoprotein/proteoglycan antigen present on melanoma. Another is NR-LU-10 that recognizes a 40 Kd glycoprotein present on lung, colon, and breast carcinomas. A third is NR-LU-11 which reacts with small cell lung carcinoma and may be used together with NR-LU-10 as "functionally specific antibodies", as described above. The maleimide group of the BSO derivative is reacted with a free sulfhydryl on an antibody to form the immunoconjugate. The reaction procedures are generally as described in U.S. Pat. No. 4,659,839. In one embodiment of the invention, the reaction procedure begins with isolation of a Fab' fragment from the antibody. This may be accomplished by conventional procedures; e.g., by first treating the antibody with papain to generate a F(ab')2 fragment (see Parham et al., *J. Immunol. Methods*, 53:133-173 [1982]). The F(ab')2 fragment is treated with a reducing agent such as dithiothreitol, 2-mercaptoethanol, or cysteine under mild reducing conditions to preferentially cleave the single disulfide bond between the two heavy chains without breaking the disulfide bonds between heavy and light chains. The two resulting Fab' fragments each have at least one free sulfhydryl group. These Fab' fragments are reacted with the derivatized BSO compound in a suitably buffered solution under conditions that will not damage the antibody fragment. Suitable buffers include such nontoxic buffers as sodium phosphate buffer, phosphate buffered saline, and sodium bicarbonate buffers, advantageously at a concentration of about 1.0 M and a pH near about 7.0. The resulting immunoconjugate is represented by the following formula 7 in which Ab represents the antibody fragment:

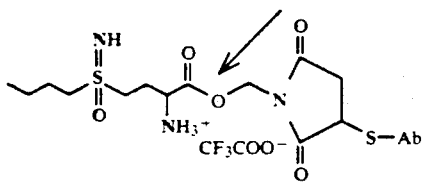

The immunoconjugate is believed to be cleaved at the bond indicated by the arrow by esterases inside the target cells. The BSO is released inside the cell in its native free form, since the carboxyl group on the drug is expected to be regenerated after release.

EXAMPLE II

In Vitro Assay of Sensitizer-Antibody Conjugate

The effectiveness of BSO as a sensitizing agent when delivered to target cells by an antibody is evaluated in an in vitro assay. The NR-LU-10-BSO conjugate in excess is incubated with a human lung carcinoma cell line, for 4–72 hours. The cytotoxic agent doxorubicin is added to the cultures at diminishing concentrations [1, 10, 100 ng/ml and 1, 10, 100 ug./ml] for 1-24 hours. A control culture, not pretreated with NR-LU-10-BSO, and another control treated with unconjugated NR-LU-10, were also incubated with doxorubicin at the same concentration. The NR-LU-10-BSO pretreated cells should be more sensitive to the doxorubicin than the controls. Antigen-negative (i.e., non-target) cells should not demonstrate enhanced killing by doxorubicin.

EXAMPLE III

Use of BSO-Antibody Conjugates in Tumor Therapy

The BSO-antibody conjugate is administered to patients with a tumor recognized by the antibody. After a suitable interval, doxorubicin is administered systemically. The patient's tumor cells should be selectively rendered more sensitive to doxorubicin than they are without the BSO-antibody treatment.

The NR-LU-10-BSO conjugate prepared as described in Example I is administered to a patient with small cell lung cancer (SCLC) following the preinjection of unconjugated NR-LU-10 (7.5 mg) to reduce binding of the NR-LU-10-BSO conjugate to cross-reactive sites in vivo, according to the methods described in copending patent application U.S. Ser. No. 07/107,136, filed Oct. 9, 1987. After a suitable period for localization, internalization, and gluthione level reduction, doxorubicin is infused. Eradication of the target (cancer) cells is expected to be enhanced compared to SCLC patients who did not receive the NR-LU-10-BSO conjugate as a sensitizer.

EXAMPLE IV

Use of Immunoconjugate Comprising a Cytotoxic Agent

The procedures of Examples II and III are repeated, except a doxorubicin-NR-LU-10 conjugate is employed instead of the free drug. The doxorubicin is attached to the antibody using any suitable linker or chemical reaction procedure. The procedures described in U.S. Pat. Nos. 4,680,388 or 4,263,279 may be used, for example. Preferably, a doxorubicin-NR-LU-11 conjugate is employed, since NR-LU-10 (to which the sensitizer is attached) and NR-LU-11 do not cross-react with any of the same normal tissues except thyroid, as far as is known. Thus the chances of delivery of both the sensitizer and the cytotoxic agent to the same normal cells through cross-reactivity are minimized. Antigen-positive cells in vitro and tumors in vivo are expected to be selectively eradicated compared to non-target cells, due to enhanced sensitivity of only the antigen-positive cells toward the cytotoxic drug.

EXAMPLE V

Synthesis Scheme for Attaching Misonidazole to Antibody via a Cleavable Linker

Figure 2:
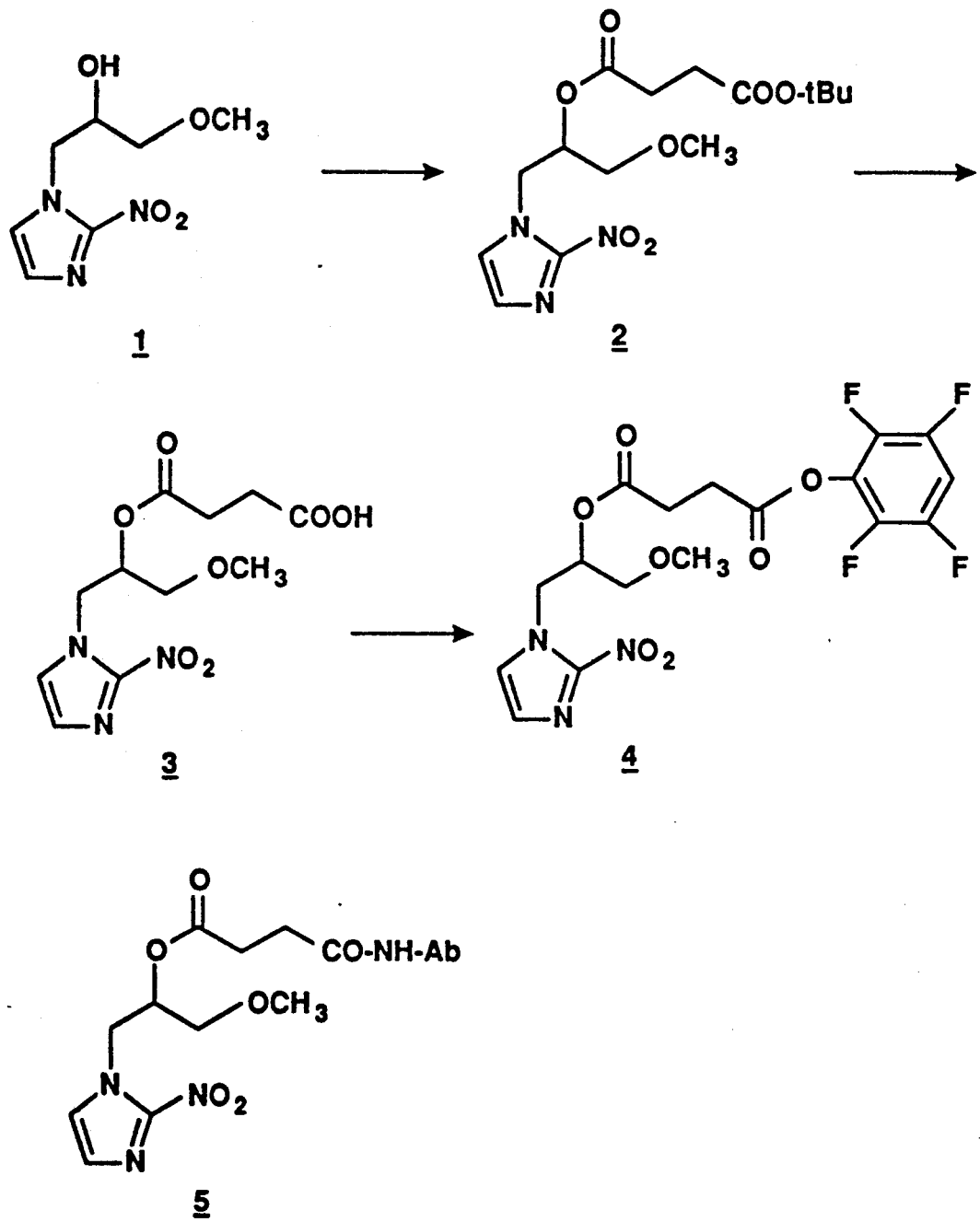
FIG. 2 depicts a synthesis scheme for linking the sensitizer misonidazole to an antibody.

The sensitizing agent misonidazole is attached to an antibody as follows, and as shown in the synthesis scheme depicted in FIG. 2.

Misonidazole-(γ-tert-butoxycarbonyl)butyrate 2: To a solution of misonidazole 1 (1 mmol) in 5 mL of dimethylformamide is added 1 mmol of succinic acid mono-tert-butyl ester in 5 mL of dimethylformamide followed by 1.1 mmol of N,N'-dicyclohexylcarbodiimide. After stirring the mixture overnight at room temperature, the precipitated solid is filtered and the filtrate evaporated. The residue is dissolved in ethyl acetate and washed successively with water and 5% bicarbonate. Ethyl acetate is removed under vacuum and the product is purified by flash chromatography over silica gel column.

Misonidazole-(γ-carboxy)butyrate 3: A solution of the above t-butyl ester 2 (1 mmol) in 5 mL of arhydrous trifluoroacetic acid is stirred at room temperature for 5-6 hours and the reaction is followed by thin layer chromatography. The solvent is removed by evaporation and the product is isolated by trituration with ether. The trifluoroacetate salt is dried in vacuo overnight before proceeding to the next step.

Misonidazole-(γ-2,3,4,5-tetrafluorophenoxycarbonyl)butyrate 4: To a solution of the above acid 3 (1 mmol) in 5 mL of anhydrous dimethylformamide, 3 mmol of N-methyl morpholine is added and the solution is cooled to from 0° to −5° C. To this solution isobutylchloroformate (1 mmol) is added and the solution is stirred for 30 mns. A solution of 2,3,5,6-tetrafluorophenol (1 mmol in 2 mL of dimethylformamide) previously cooled to 0° to −5° C. is added in drops over a period of 5-10 mns. After about an hour at this temperature, the mixture is allowed to come to ambient temperature. The solvents are removed in vacuo and the residue is dissolved in ethyl acetate (10-15 mL) and washed with water. The solvent is removed and the product is isolated by flash chromatography on a silica gel column. Final purification is carried out by liquid chromatography in a normal phase column.

The misonidazole derivative 4 is combined with an antibody under physiologically acceptable conditions so that the antibody is not damaged. The tetraflurophenyl ester group on the misonidazole derivative compound reacts with the free amine group of a lysine residue on the antibody to form an amide bond, thereby forming an iumunoconjugate. The reaction conditions are generally as described in Example I above.

The resulting immunoconjugate has the following formula 5, where Ab represents the antibody:

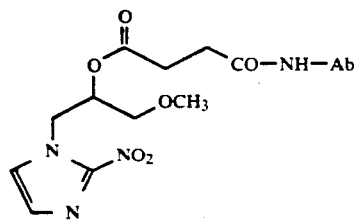

Intracellular esterases are believed to cleave the immunoconjugate at the position shown by the arrow. Misonidazole is released inside the target cells in its native free form, since the hydroxyl group on the drug is regenerated.

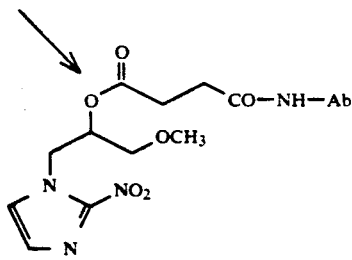

EXAMPLE VI

Use of Misonidazole as a Sensitizer in Combination with Radiotherapy

A misonidazole—NR-ML-05 immunoconjugate prepared in accordance with Example V is employed in an in vitro assay and administered to melanoma patients as described in examples II and III above, except that the cytotoxic agent used is $^{188}$Re instead of doxorubicin. The metal radionuclide is in the form of an 188Re chelate-antibody fragment conjugate having the following structural formula wherein Ab represents the antibody fragment:

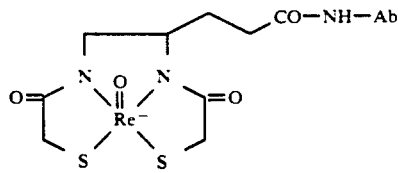

This $^{188}$Re-containing immunoconjugate is prepared as described in European Patent Application Publication No. 188,256 or in copending U.S. patent application Ser. No. 065,011 Sodium perrhenate (3 mL, 15 mCi, produced from a W-188/Re-188 research scale generator) was added to a vial containing a lyophilized mixture comprising citric acid, 75 mg; stannous chloride, 0.75 mg; gentisic acid, 0.25 mg; and lactose, 100 mg. The vial was agitated gently to mix the contents, then incubated at room temperature for 10 minutes to form a 188Re-citrate exchange complex. Next, 0.50 mL of isopropyl alcohol was added to a separate vial containing 0.50 mg of 2,3,5,6-tetrafluorophenyl-4,5-bis[S-(1-ethoxyethyl)thioacetamido]pentanoate, which is a diamide dimercaptide chelating compound comprising ethoxyethyl sulfur protective groups and a 2,3,5,6-tetrafluorophenyl ester group, having the formula:

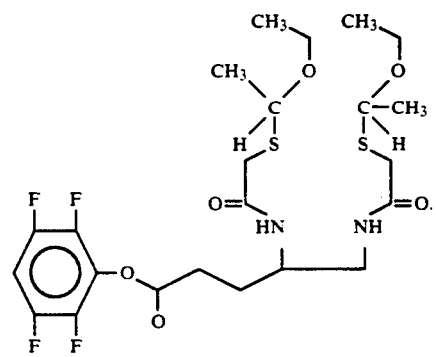

The vial was agitated for two minutes to completely dissolve the chelating compound Next, 0.30 mL of this solution was transferred to the vial containing the $^{188}$Recitrate complex prepared above After gentle mixing, the vial was incubated in a 75° C.±2° C. water bath for 15 minutes, then immediately transferred to a 0° C. ice bath for two minutes The yields of $^{188}$Re-labeled chelate then ranged between 75% and 90% as measured by reversed phase $C_{18}$ HPLC analysis.

A column containing a $C_{18}$ reversed phase low-pressure material (Baker $C_{18}$ cartridges) was used to purify the $^{188}$Re-labeled chelate. After conditioning of the cartridge with ethanol and water, the sample was loaded and washed with three times 2 mL of water and three times 2 mL of 20% ethanol/0.01 M phosphate buffer. The column was then dried in vacuo and eluted with two times 1.0 mL acetonitrile. About 75% of the $^{188}$Re-radioactivity was recovered in greater than 95% purity as the ester chelate compound. The organic solvent was then evaporated under a flow of inert gas.

The chelate is then conjugated to a Fab fragment of the anti-melanoma monoclonal antibody designated 9.2.27 (described above). The Fab fragments are generated by papain treatment according to conventional procedures. A buffered solution of the antibody fragment (5 mg/mL, 0.5 mL) is added to the purified $^{188}$Re-labeled chelate, followed by 0.5 mL of 0.5 M carbonate/bicarbonate buffer pH 9.50. The reaction is kept at room temperature for 15 minutes, then 25 mg of L-lysine, 0.1 mL, is added and the reaction is pursued at room temperature for 15 minutes more. The tetrafluorophenyl ester group of the chelate reacts with a free amine group on the antibody fragment to form an amide bond.

A column containing Sephadex G-25 material is used to purify the $^{188}$Re-labeled immunoconjugate. The reaction mixture is loaded on top of the column, and 1.2 mL aliquots are collected using PBS buffer to rinse the reaction vial and elute the $^{188}$Re immunoconjugate in the third and fourth fractions.

The immunoconjugate is then further diluted with PBS, and radioactivity is measured prior to injection into a melanoma patient. Prior to injection of the immunoconjugate comprising the cytotoxic radioisotope, the misonidazole-NR-ML-05 immunoconjugate is administered as a sensitizer. The $^{188}$Re-N$_2$S$_2$ chelate-9.2.27 immunoconjugate then is administered at its maximum tolerated dose. The misonidazole sensitizer is expected to enhance the effectiveness of the radioisotope in destroying melanoma cells. Toxicity toward normal cells is reduced through the use of immunoconjugates which selectively deliver the sensitizer and the metal radionuclide to the target melanoma cells.

EXAMPLE VII

Use of WR 2721 to Protect the Bone Marrow and Other Normal Organs from the Effects of Radiolabeled Antibodies WR 2721 is administered to a patient with colon cancer intravenously. The dose may be 0.2 to 2 gm/m$^2$ but a range of 0.5 to 1 gm/m$^2$ is preferred. The drug may be given only once, or daily, or several times daily to effect the best marrow protection without compromising the sensitivity of the tumor.

NR-Co-02, a murine monoclonal antibody that reacts with a variant of carcinoembryonic antigen (CEA), is digested with papain and the F(ab')$_2$ fragment isolated by ion exchange chromatography. The antibody fragment is labeled with rhenium-186 by attaching a $^{186}$Re labeled N$_2$S$_2$ chelate to the antibody fragment as described in Example VI. The NR-Co-02/rhenium-186 conjugate is injected intravenously into the patient with metastatic colon cancer who had received WR 2721 0–12 hours earlier, preferably 0–10 minutes earlier. The dose of Re-186 may vary from 50–1000 mCi on 1 to 500 mg NR-Co-02, preferably 10–200 mg.

The effect on the bone marrow is monitored by peripheral blood counts (hemaglobin, leukocyte, and platelet counts). Patients who receive WR 2721 have less decrease in one, two, or all three of these blood counts for a given dose of Re-186 than patients who receive the radiolabeled antibody alone without having received WR 2721.

EXAMPLE VIII

Conjugating the Drug WR 2721 to an Antibody

The drug WR 2721 is represented by the following formula:

H$_2$N—(CH$_2$)$_3$—NH—(CH$_2$)$_2$—SPO$_3$H$_2$

The drug is reacted with p-carboxybenzaldehyde to produce a derivative of the following formula, formed by reaction of the —NH$_2$ group on the drug with the aldehyde group of p-carboxybenzaldehyde:

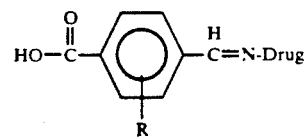

wherein R is defined below.

The carboxylic acid group of the derivative is reacted with a free amine group on a lysine residue of a targeting protein, using a water soluble carbodiimide coupling reagent. The resulting WR 2721—targeting protein conjugate is of the formula:

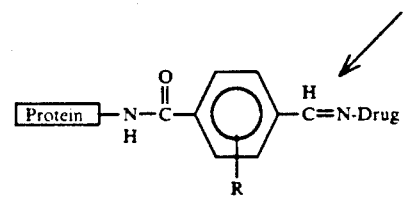

The arrow indicates a bond that is cleavable in vivo. The substituent R on the benzene ring is an electron withdrawing group that is optional, but the presence of such an R group will make the cleavable bond more susceptible to cleavage in vivo. Suitable substituents R include, but are not limited to, F, Cl, —NO$_2$, and CF$_3$, and the benzene ring may have one or more R groups attached thereto. Derivatives of p-carboxybenzaldehyde comprising such substituents may be reacted with the drug to produce WR 2721 derivatives comprising such substituents R.

EXAMPLE IX

Use of WR 2721 Antibody Conjugates to Protect Bone Marrow from the Toxicity Associated with Cytotoxic Agents WR 2721/antibody conjugates are used to selectively protect bone marrow from the toxicity of systemic chemotherapy, external beam radiation therapy, including TBI, and radiolabeled or drug or toxin conjugates of antibodies, fragments thereof, or other targeting agents. WR 2721 is conjugated to an antibody designated NR-ST-10, using the procedures of Example VIII. NR-ST-10 is an antibody reactive with bone marrow stem cells. This conjugate is administered to a patient with colon cancer at a dose of 0.001–1 gm/m$^2$, preferably 0.02–0.5 gm/m$^2$. Subsequently, 0–24 hours later, but preferably 0–6 hours later, chemotherapy, external beam radiation therapy, or radiolabeled NR-Co-02 (see Example VII) or a drug conjugate of NR-Lu-10, or a toxin conjugate of NR-Lu-10, or some or all of these are administered to the patient. The chemotherapeutic drug is cisplatin or an alkylating agent such as a nitrogen mustard, for example. The WR 2721, selectively delivered to the stem cell, protects the marrow, measured as in Example VII. The tumor is not affected by WR 2721 since the drug is delivered selectively to the marrow stem cell by the antibody.

What is claimed is:

1. A conjugate represented by the following formula:

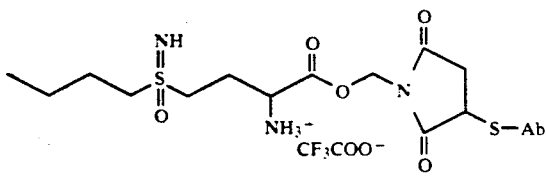

wherein Ab represents an antibody or antibody fragment.

2. The conjugate of claim 1 wherein the antibody or antibody fragment is a monoclonal antibody or a fragment thereof.

3. The conjugate of claim 2 wherein the monoclonal antibody or fragment thereof is specific for cancer cells.

4. The conjugate of claim 3 wherein the monoclonal antibody is chosen from the group consisting of NR-ML-05, anti-TAC, NR-LU-10, NR-LU-11 and OVB$_3$.

5. The conjugate of claim 1 wherein the conjugate additionally comprises a cytotoxic agent linked to the same antibody molecule.

6. A conjugate comprising a drug WR 2721 or a functionally equivalent derivative or analog thereof bound to a targeting protein.

7. The conjugate of claim 6 wherein said conjugate has the formula:

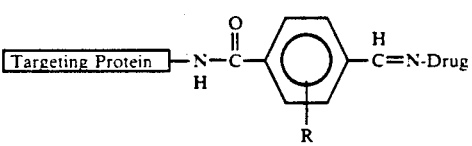

wherein R is an optional substituent on the benzene ring and R represents one or more electron withdrawing groups on the benzene ring.

8. The conjugate of claim 6 or 7 wherein the targeting protein is a monoclonal antibody or fragment thereof.

9. A conjugate of the following formula:

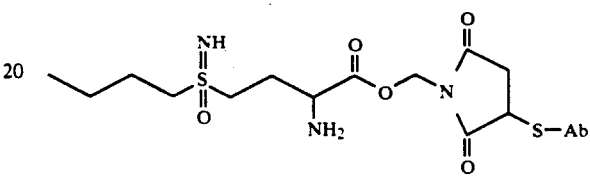

wherein Ab represents an antibody or antibody fragment.

* * * * *